United States Patent
Klingenberg et al.

(10) Patent No.: US 9,842,191 B2
(45) Date of Patent: Dec. 12, 2017

(54) IMAGING SYSTEM OPERATIONAL PROPERTY MONITORING

(71) Applicant: KONINKLIJKE PHILIPS N.V., Eindhoven (NL)

(72) Inventors: Edmund Walter Klingenberg, Chardon, OH (US); Jorge Ivan Zapata Arias, Chagrin Falls, OH (US); Frans Van Duijnhoven, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/910,021

(22) PCT Filed: Aug. 4, 2014

(86) PCT No.: PCT/IB2014/063680
§ 371 (c)(1),
(2) Date: Feb. 4, 2016

(87) PCT Pub. No.: WO2015/019273
PCT Pub. Date: Feb. 12, 2015

(65) Prior Publication Data
US 2016/0188828 A1 Jun. 30, 2016

Related U.S. Application Data
(60) Provisional application No. 61/862,982, filed on Aug. 7, 2013.

(51) Int. Cl.
*G08B 21/00* (2006.01)
*G06F 19/00* (2011.01)
(Continued)

(52) U.S. Cl.
CPC ........ *G06F 19/3412* (2013.01); *A61B 6/586* (2013.01); *H04N 17/002* (2013.01)

(58) Field of Classification Search
CPC ....... A61B 6/032; A61B 5/0022; A61B 5/002; A61B 5/0015; A61B 5/0002; A61B 6/586;
(Continued)

(56) References Cited

U.S. PATENT DOCUMENTS 6,473,569 B1 10/2002 Shah et al.
7,127,371 B2 * 10/2006 Duckert ............... G06F 19/3412
324/383
(Continued)

OTHER PUBLICATIONS

Tsao, et al., "Trend analysis on system error files", International Symposium on Fault Tolerant Computing Systems, Jun. 1, 1983.
(Continued)

*Primary Examiner* — Thomas Mullen

(57) ABSTRACT

This invention relates to an imaging system and more particularly to imaging system operational property monitoring and describes an approach that makes key parameters available remotely from a collection of imaging systems for trending, ranking, analysis and further service telemetry. A method includes obtaining a set of operational properties of an imaging system. The method further includes identifying an operational property of the set of operational properties that intermittently falls outside of a predetermined operational range and does not require immediate service of the imaging system. The method further includes generating a trend for the identified operational property. The method further includes comparing the generated trend with at least one reference trend. The method further includes determining the imaging system should be serviced based on the comparison. The method further includes generating a service notification signal in response to determining the imaging system should be serviced, where the service notification signal invokes service of the imaging system.

23 Claims, 3 Drawing Sheets

(51) Int. Cl.
*A61B 6/00* (2006.01)
*H04N 17/00* (2006.01)

(58) Field of Classification Search
CPC ............... G06F 19/321; G06F 19/3418; G06F 19/3412; G06Q 50/22; H04N 17/002
USPC ......... 340/540, 870.09, 870.16, 870.17, 526, 340/527, 529, 584, 588, 589, 679
See application file for complete search history.

(56) References Cited

U.S. PATENT DOCUMENTS

| | | |
|---|---|---|
| 2003/0216888 A1 | 11/2003 | Ridolfo |
| 2005/0114892 A1 | 5/2005 | Chan et al. |
| 2006/0277446 A1 | 12/2006 | Ikeno |
| 2011/0121969 A1 | 5/2011 | Mercer et al. |
| 2013/0086208 A1 | 4/2013 | Heine et al. |

OTHER PUBLICATIONS

Salfner, et al., "A survey of online failure prediction methods", AMC Computing Surveys, vol. 42, No. 3, Mar. 1, 2010.

* cited by examiner ured as limiting the invention.

IMAGING SYSTEM OPERATIONAL PROPERTY MONITORING

CROSS REFERENCE TO RELATED APPLICATIONS

This application is the U.S. National Phase application under 35 U.S.C. §371 of International Application No. PCT/IB2014/063680, filed Aug. 4, 2014, published as WO 2015/019273 on Feb. 12, 2015, which claims the benefit of U.S. Provisional Patent Application No. 61/862,982 filed Aug. 7, 2013. These applications are hereby incorporated by reference herein.

BACKGROUND

The following generally relates to an imaging system and more particularly to imaging system operational property monitoring. However, the following is also amenable to non-imaging systems.

Service telemetry and remote monitoring of complex patient imaging devices may require control of key functionality and performance parameters to ensure system availability to execute clinical protocols on imaging subjects while in a clinical setting. Having remote visibility of these key parameters and functionality, coupled with remote access to governing subsystems as needed, could prevent hard failures that might render the unit unusable thus limiting the patient throughput.

The capability to use such information for telemetry and further analysis requires data transfer from units installed across geographies to a dedicated control center(s) and processing of such data to extract and discern specific information to accomplish the objective of remote monitoring. One way to accomplish the above mentioned process is to operate on large volumes of log files extracted from the device. This typically requires significant data transmission bandwidth, significant control center computing and storage capacity, and dedicated man power to execute analysis and act upon data computing results.

Another way is to directly extract certain parameters from the device log files and subsystems and send only that information up to the control center. This is a much more resource-friendly method, lending itself to improved scalability as the number of devices deployed to the field increases. Additionally, it meets business needs of protecting the device information and analysis by delivering the parameters to company proprietary control centers. These parameters can be evaluated on a remote monitoring alert server, which can identify instantly actionable values within a specified time frame.

However, some parameters only become actionable when their out-of-threshold values persist over a longer period of time. Unfortunately, such parameters may result in false alarms if not evaluated over time and thus require additional time to analyze and investigate from systems that are clinically functioning as designed. Therefore, there is an unresolved need for further approaches to evaluate such parameters.

SUMMARY

Aspects described herein address the above-referenced problems and others.

The following describes an approach that makes key parameters available remotely from a collection of imaging systems installed across different geographies for trending, ranking, analysis and/or further service telemetry, while overcoming network communication bandwidth and/or connectivity limitations, and a need of large capacity computing servers to analyze multi-systems information.

In one aspect, a method includes obtaining a set of operational properties of an imaging system. The method further includes identifying an operational property of the set of operational properties that intermittently falls outside of a predetermined operational range and does not require immediate service of the imaging system. The method further includes generating a trend for the identified operational property. The method further includes comparing the generated trend with at least one reference trend. The method further includes determining the imaging system should be serviced based on the comparison. The method further includes generating a service notification signal in response to determining the imaging system should be serviced, where the service notification signal invokes service of the imaging system.

In another aspect, a system includes an imaging system health monitoring system that invokes service of an imaging system based on identifying an operational property of the imaging system that intermittently and persistently falls out of a predetermined operational range, where the operational property does not require immediate service of the imaging system.

In another aspect, a computer readable storage medium encoded with computer readable instructions, which, when executed by a processor, cause the processor to: identify an operational property of a set of operational properties that intermittently falls outside of a predetermined operational range and does not require immediate service of the imaging system, generate a trend for the identified operational property, compare the generated trend with at least one reference trend, determine the imaging system should be serviced based on the comparison, generate a service notification signal in response to determining the imaging system should be serviced, and invoke service of the imaging system in response to the service notification signal.

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
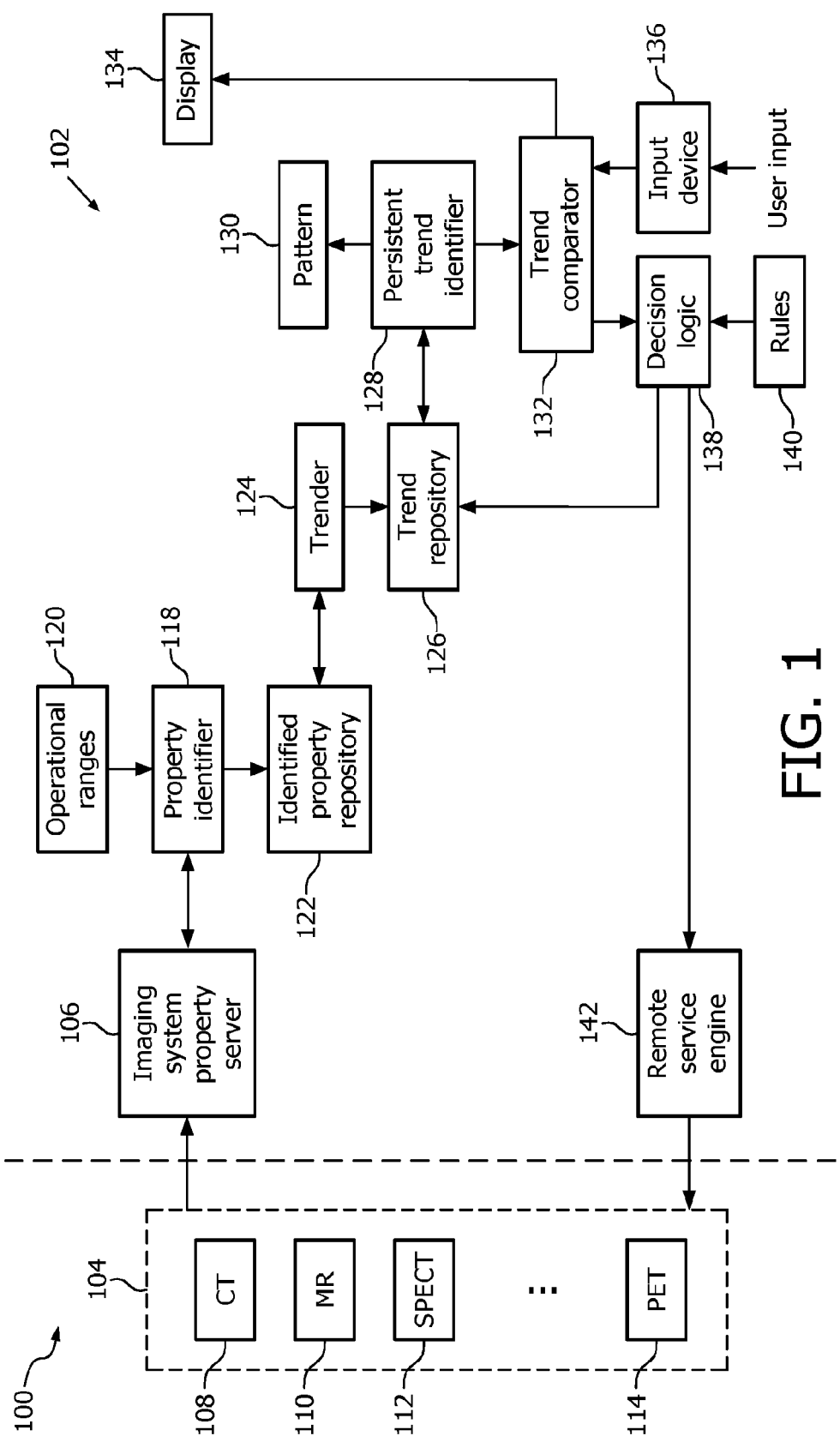
FIG. 1 schematically illustrates an imaging system health monitoring system in connection with a plurality of imaging and/or non-imaging systems.

FIG. 1 schematically illustrates a system 100, which includes an imaging system health monitoring system 102 and a set of imaging systems 104.

An imaging system property server 106 obtains operational properties of one or more of the set of imaging systems 104. Examples of suitable imaging systems 104 include, but are not limited to, computed tomography (CT) scanner 108, a magnetic resonance (MR) scanner 110, a single photon emission computed tomography (SPECT) scanner 112, and a positron emission tomography (PET)

scanner 114. The operational property may include and/or be associated with an identifier that identifies the particular imaging system 104.

Examples of the operational properties include, but are not limited to, temperature values at one or more predetermined locations, temperature values of one or more predetermined hardware components, electrical values (e.g., voltages, currents, impendences, etc.) of one or more predetermined components or circuits, percentage of disc space available, data transfer issues, data transfer failures, image quality metrics, and/or other properties. Such operational properties can be measured and/or otherwise determined by hardware and/or software at the systems 104.

Generally, an obtained operational property is represented as a numerical value. For example, a property representing a temperature of a particular component could be in the form of an analog or digital value representing the temperature (e.g., a digital value representing 70 degrees). Examples of image quality properties includes noise (e.g., standard deviation, variance, etc.), resolution (e.g., expressed in line pairs per millimeter, LP/mm), artifact (e.g., a binary value representing presence or absence thereof), a ratio value of detector image uniformity of image data, a tracking of a center of rotation of detectors on the imaging system, a spatial resolution performance of the imaging system, a sensitivity performance of the imaging system, and/or other image quality properties that can be represented in a numerical value.

In one non-limiting instance, the imaging system property server 106 polls one or more of the systems 104 for such operational properties. Such polling can be based on a predetermined schedule (e.g., every night, etc.), on demand (e.g., in response to a signal indicating a user request to poll), and/or otherwise. Additionally or alternatively, a system 104 can push or transmit the one or more operational properties to the imaging system property server 106. The pushing can be based on a predetermined schedule (e.g., every night, etc.), on demand (e.g., in response to a signal indicating a user request to poll), etc.

The imaging system property server 106 can be part of the imaging system health monitoring system 102 (as shown), separate therefrom, and/or distributed between the imaging system health monitoring system 102 and one or more other systems. An example of a system separate therefrom includes, but is not limited to, one or more of the imaging systems 104, a facility at which an imaging system 104 is located, a centralized server for the imaging systems 104, etc.

A property identifier 118 identifies certain operational properties stored by the imaging system property server 106. In the illustrated embodiment, the certain operational properties are those with values that intermittently fall outside of operational ranges 120 while the particular imaging system 104 is still operational and functional to perform the service it provides (e.g., scan a subject or object). Such operational properties are in contrast to those (e.g., an x-ray tube arc, a defective detector, etc.) that indicate the particular imaging system 104 requires immediate service and/or attention.

Identified property storage 122 stores the property values of the identified properties. The properties' values may be measured continuously or periodically. In either instance, all of the identified properties or a subset thereof are stored. For the latter case, for example, an average value over one or more time ranges may be obtained instead of all of the values. In another example, just a maximum and/or just a minimum value over the one or more time ranges are obtained. In yet another example, another representative value is obtained and stored.

A trender 124 generates trends for the information stored in the identified property storage 122. For example, where a temperature of a circuit board intermittently falls out of specification and the imaging system 104 still scans and produces diagnostics images, temperatures of the circuit board may be stored in the identified property storage 122 and trended over time by the trender 124. By way of another example, where an image quality value intermittently falls out of specification, the value may be stored in the identified property storage 122 and trended over time by the trender 124.

A trend repository 126 stores the trends generated by the trender 124. The trend repository 126 can be part of the imaging system health monitoring system 102 (as shown), separate therefrom, and/or distributed between the imaging system health monitoring system 102 and one or more other systems.

A persistent trend identifier 128 identifies trends in the trend repository 126 in which the falling of the property out of specification persists over a predetermined time frame. In one instance, this is achieved by periodically evaluating the trends in the trend repository 126 for a predetermined pattern 128 (e.g., a threshold number of times over a particular time period). Trends that fail to meet the pattern 128 can be removed from the trend repository 126.

A trend comparator 132 compares identified persistent trends with other trends. For example, in one instance, the trend comparator 132 compares the identified persistent trends with trends of imaging systems that have and/or had the same persistent property but did not require service. Additionally or alternatively, the trend comparator 132 compares the identified persistent trends with trends of imaging systems that have and/or had the same persistent property and required service.

Additionally or alternatively, the trend comparator 132 compares the identified persistent trends with previously generated trends for the same imaging system and the same persistent property. From this, the trend comparator 132 can determine whether the intermittent property is occurring intermittently more frequently, less frequently or the same. Other comparisons are also contemplated herein.

The comparison can be invoked by, and based upon, a signal indicative of a user input, such as a signal indicative of a user-selected comparison trend. Additionally or alternatively, the persistent trend identifier 128 can automatically identify a trend for the comparison. In the latter instance, the identified trend may need to be confirmed or verified by a user and/or the user can override an automatically selected trend.

The trends and/or comparisons can be visually displayed via a display 134. For display purposes, the trends and/or comparisons can be ranked based on a predetermined priority, which may take into account the particular property, the type of the imaging system, the degree of persistence, etc. Indicia such as color, character size, background, and/or other indicia can be utilized to emphasize, highlight, rank, etc. the displayed trends and/or comparisons.

An input device 136 can be used to obtain a signal indicative of a user input. Examples of input devices include, but are not limited to, a mouse, a touch screen, a digital pen, a microphone, etc. In one instance, the signal may flag a trend for further evaluation and/or service. In another instance, the signal may flag a trend as requiring no further evaluation and/or service.

Decision logic 138 evaluates the trends and/or trend comparisons based on a set of predetermined rules 140. This includes taking into account the signal indicative of a user input, where such a signal has been provided. Where a rule 140 indicates that an imaging system 104 does not require service, the decision logic 138 may associate and/or append the trend with an explanation indicating the reason for this decision and store the appended trend in the trend repository 126 for subsequent analysis and/or archiving.

Where a rule indicates that the imaging system 104 should be serviced, a notification signal is generated by the decision logic 138 and transmitted by the decision logic 138. Optionally, the decision logic 138 may associate and/or append the trend with an explanation indicating the reason for this decision and store the appended trend in the trend repository 126. The rules 140 can be predetermined and/or user configurable.

A remote service engine 142, in response to receiving a notification signal and if the service can be performed remotely by the remote service engine 142, accesses the imaging system 104 with the property with the persistent trend and performs service, which may include human interaction or may not include any human interaction. Additionally or alternatively, the remote service engine 142 provides an electronic notification to service personnel, which may result in on-site servicing of the imaging system 104.

Generally, the imaging system health monitoring system 102 makes key parameters available remotely from a collection of imaging systems 104 installed across different geographies for trending, ranking, analysis and/or further service telemetry, while overcoming network communication bandwidth and/or connectivity limitations, and a need of large capacity computing servers to analyze multi-systems information.

It is to be appreciated that at least a sub-portion of the imaging system health monitoring system 102 can be implemented via one or more computer processors (e.g., a central processing unit (CPU), a microprocessor, etc.) executing one or more computer executable instructions embedded or encoded on computer readable storage media, which excludes transitory media, such as physical memory. However, at least one of the computer executable instructions can alternatively be carried by a carrier wave, signal, and other transitory media and implemented via the one or more computer processors.

Figure 2:
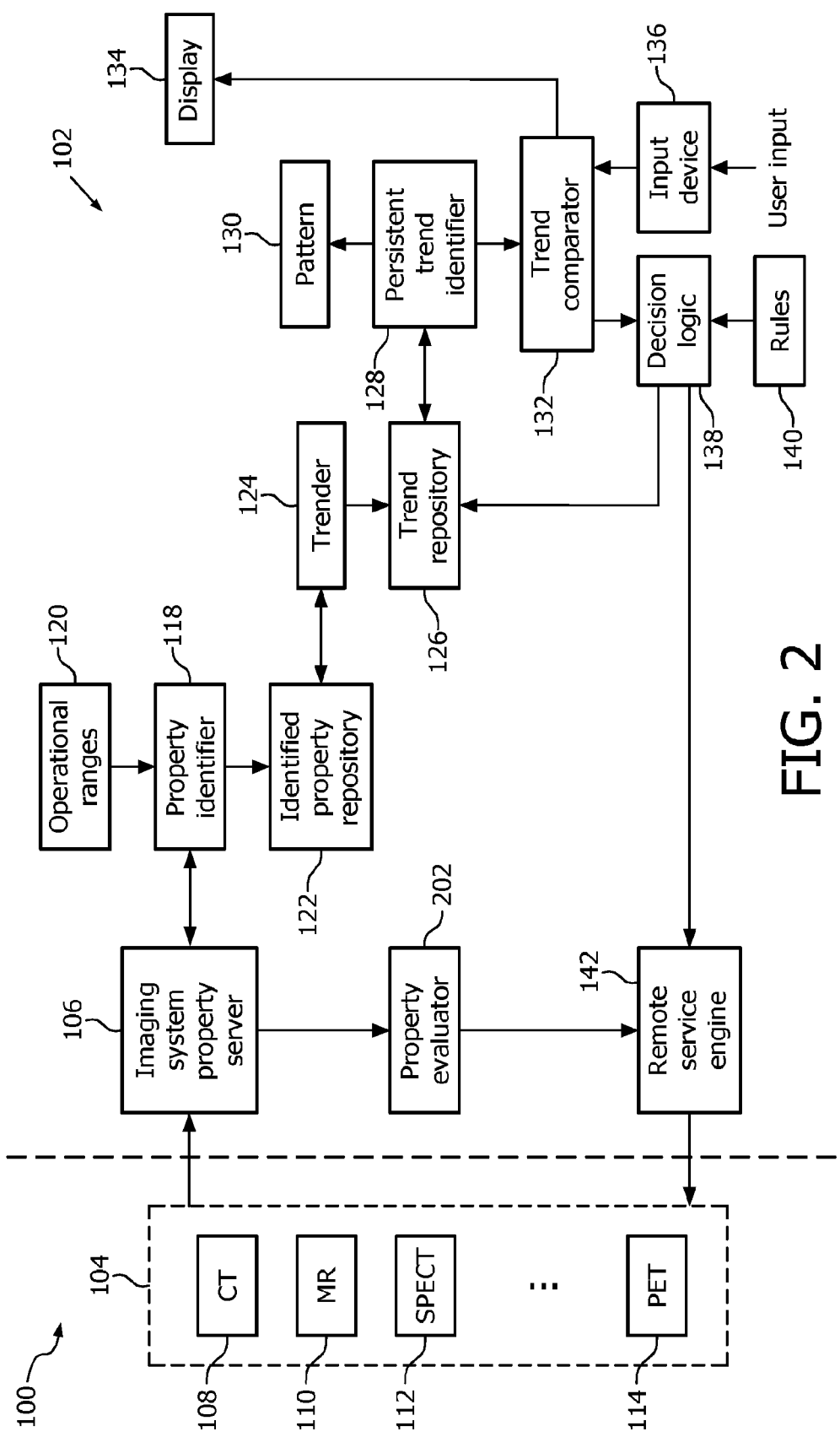
FIG. 2 schematically illustrates a variation of the imaging system health monitoring system of FIG. 1.

FIG. 2 schematically illustrates a variation of the system 100 in which the imaging system health monitoring system 102 further includes a property evaluator 202 that evaluates the operational properties in the imaging system property server 106, and, in response to identifying an operational property which indicates an imaging system 104 requires immediate service and/or attention, notifies the remote service engine 142 as such, as indicated herein and/or otherwise.

Figure 3:
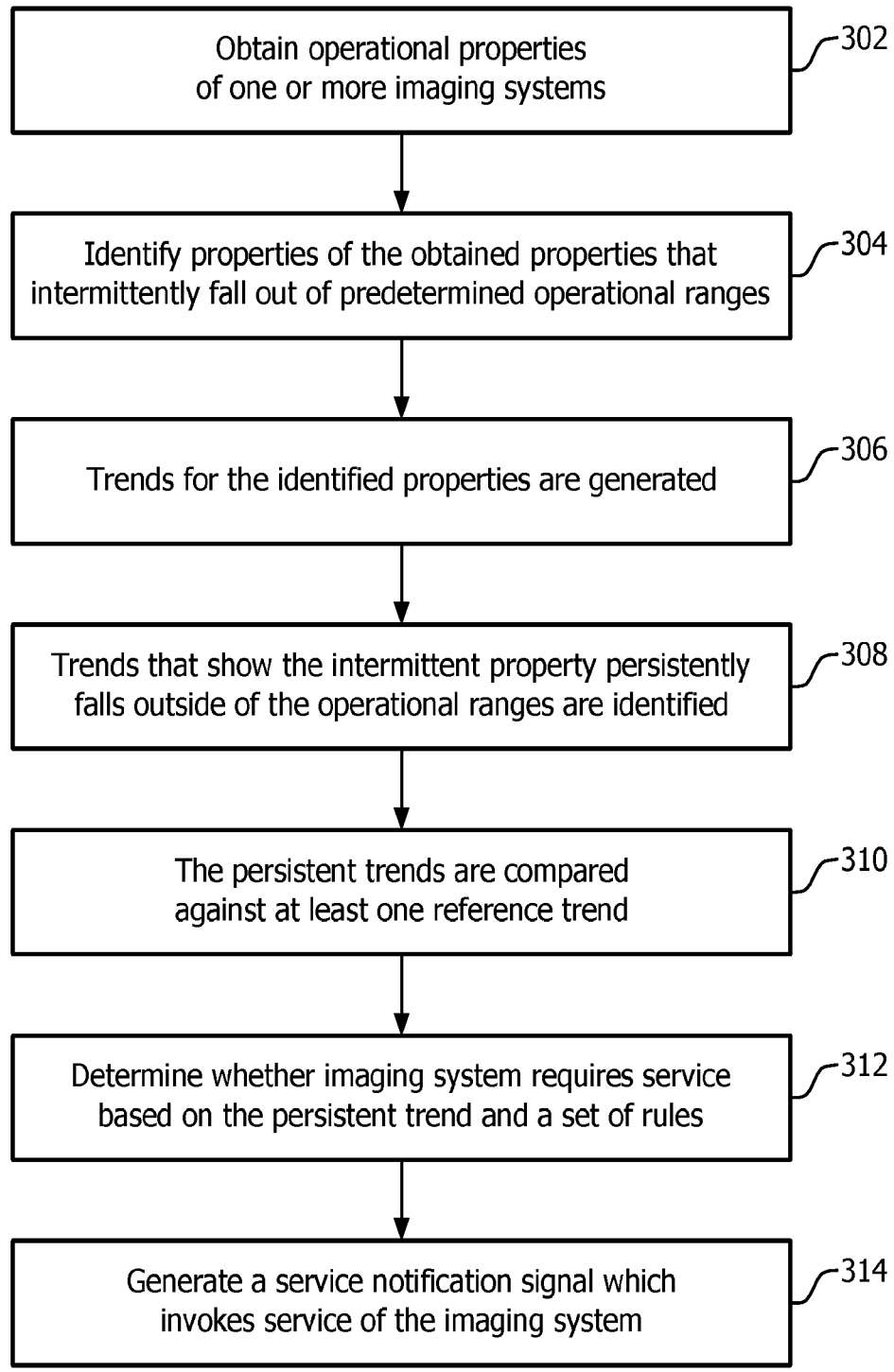
FIG. 3 illustrates a method in accordance with the embodiments disclosed herein.

FIG. 3 illustrates example method in accordance with the embodiment discussed herein.

It is to be appreciated that the ordering of the acts of these methods is not limiting. As such, other orderings are contemplated herein. In addition, one or more acts may be omitted and/or one or more additional acts may be included.

At 302, operational properties of one or more imaging systems are obtained. As discussed herein, the operational properties can be obtained through pulling and/or pushing of the properties, and are numerical values.

At 304, properties of the obtained properties which intermittently fall out of predetermined operational ranges are identified.

At 306, trends for the identified properties which intermittently fall out of predetermined operational ranges are generated.

At 308, generated trends in which the property persistently falls out of the predetermined operational ranges are identified. In one non-limiting instance, this includes ranking the categories (e.g., groups of properties) based on health (e.g., good, suspect, unhealthy, etc.) and displaying them using indicia, such as color, background, etc., which visually shows which subsystems are healthy, suspect, unhealthy, etc. Generally, displaying the health of the identified systems can provide a picture of the overall health of a system type within the installed base.

At 310, the persistent trends are compared with one or more reference trends. This includes trends of the same property of a different imaging system which resulted in service of the different imaging system, trends of the same property of a different imaging system which did not result in service of the different imaging system, trends of the same property of the imaging system, etc.

At 312, it is determined whether the imaging system with a property that persistently falls out of the predetermined operational ranges is to be serviced based on a set of rules.

If so, at 314, a service notification signal is generated and transmitted. As discussed herein, the service notification signal may result in service of the imaging system.

The above acts may be implemented by way of computer readable instructions, encoded or embedded on computer readable storage medium, which, when executed by a computer processor cause the processor to carry out the described acts. Additionally or alternatively, at least one of the computer readable instructions is carried by a signal, carrier wave and other transitory medium and implemented by the computer processor.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   obtaining a set of operational properties of an imaging system;
   identifying an operational property of the set of operational properties that intermittently falls outside of a predetermined operational range and does not require immediate servicing of the imaging system;
   generating a trend for the identified operational property;
   comparing the generated trend with at least one reference trend;
   determining that the imaging system should be serviced based on the comparison; and
   generating a servicing notification signal in response to determining that the imaging system should be serviced, where the servicing notification signal invokes servicing of the imaging system.

2. The method of claim 1, wherein obtaining the set of operational properties includes determining a set of numerical values, each numerical value representing a corresponding one of the operational properties of the set of operational properties.

3. The method of claim 2, wherein the set of operational properties includes an image quality metric.

4. The method of claim 3, wherein the numerical value represents a standard deviation for at least a sub-set of voxels of image data generated by the imaging system.

5. The method of claim 3, wherein the numerical value represents a resolution of least a sub-set of voxels of image data generated by the imaging system.

6. The method of claim 3, wherein the numerical value is a binary value.

7. The method of claim 1, wherein the identified operational property includes one or more of a temperature, an electrical characteristic, a state of data storage, or a data transmission rate.

8. The method of claim 1, wherein the reference trend includes a trend for a different imaging system with the same operational property intermittently falling outside of the predetermined range but not requiring servicing.

9. The method of claim 1, wherein the reference trend includes a trend for a different imaging system with the same operational property intermittently falling outside of the predetermined range and requiring servicing.

10. The method of claim 1, wherein the reference trend includes a trend for the same imaging system with the same operational property intermittently falling outside of the predetermined range, and the comparison indicates whether the intermittent operational property is occurring more frequently or less frequently.

11. The method of claim 1, further comprising:
receiving a signal indicative of a user input indicating the imaging system is to be serviced; and
generating the servicing notification signal in response to receiving the signal.

12. A system comprising:
an imaging system health monitoring system that determines whether an imaging system should be serviced based on identifying an operational property of the imaging system that intermittently and persistently falls out of a predetermined operational range.

13. The system of claim 12, the imaging system health monitoring system comprising:
a property identifier that identifies the operational property;
a trender that generates a trend for the identified operational property;
a trend comparator that compares the generated trend with at least one reference trend; and
decision logic that determines whether the imaging system should be serviced based on the trend comparison and that generates a servicing notification signal when the imaging system should be serviced.

14. The system of claim 13, wherein the at least one reference trend includes at least one of a first trend for a different imaging system with the same operational property intermittently falling outside of the predetermined range but not requiring servicing, a second trend for a different imaging system with the same operational property intermittently falling outside of the predetermined range and requiring servicing, or a third trend for the same imaging system with the same operational property intermittently falling outside of the predetermined range.

15. The system of claim 12, wherein the operational property is represented by a numerical value.

16. The system of claim 12, wherein the operational property is an image quality metric.

17. The system of claim 16, wherein the image quality metric includes a numerical value that represents a ratio value of detector image uniformity of image data generated by the imaging system.

18. The system of claim 16, wherein the image quality metric includes a numerical value that represents a tracking of a center of rotation of detectors on the imaging system.

19. The system of claim 16, wherein the image quality metric includes a numerical value that represents a spatial resolution performance of the imaging system.

20. The system of claim 16, wherein the image quality metric includes a numerical value that represents a sensitivity performance of the imaging system.

21. The system of claim 16, wherein the operational property includes one or more of a temperature, an electrical characteristic, a state of data storage, data transfer issues, or data transfer failures.

22. A non-transitory computer readable storage medium encoded with computer readable instructions, which, when executed by a processor, cause the processor to:
identify an operational property of a set of operational properties of an imaging system that intermittently falls outside of a predetermined operational range;
generate a trend for the identified operational property;
compare the generated trend with at least one reference trend;
determine whether the imaging system should be serviced based on the trend comparison; and
generate a servicing notification signal in response to determining that the imaging system should be serviced.

23. A monitoring system for monitoring an imaging system to determine whether the imaging system should be serviced, the system comprising:
a computer processor configured to:
identify an operational property of the imaging system that intermittently falls outside of a predetermined operational range,
generate a trend for the identified operational property,
compare the generated trend with at least one reference trend,
determine whether the imaging system should be serviced based on the trend comparison, and
generate a servicing notification signal in response to determining that the imaging system should be serviced; and
a display apparatus configured to display at least one of the generated trend and a servicing notification.

* * * * *